United States Patent [19]

Copelin

[11] 4,044,059

[45] Aug. 23, 1977

[54] ONE-STEP METHOD FOR HYDROLYZING AND HYDROGENATING ACETAL-ALDEHYDES

[75] Inventor: Harry Bugbird Copelin, Wilmington, Del.

[73] Assignee: E. I. Du Pont de Nemours and Company, Wilmington, Del.

[21] Appl. No.: 682,979

[22] Filed: May 4, 1976

Related U.S. Application Data

[63] Continuation-in-part of Ser. No. 494,292, Aug. 2, 1974, abandoned.

[30] Foreign Application Priority Data

May 30, 1975 Germany .............................. 2523840

[51] Int. Cl.² .................. C07C 27/14; C07C 31/18

[52] U.S. Cl. .................. 260/635 A; 260/346.11; 260/635 E

[58] Field of Search ........ 260/635 E, 635 A, 346.1 R

[56] References Cited

U.S. PATENT DOCUMENTS

2,888,492  5/1959  Fischer et al. ...................... 260/635

FOREIGN PATENT DOCUMENTS

824,551  12/1959  United Kingdom ................. 260/635

Primary Examiner—Henry R. Jiles
Assistant Examiner—Bernard Dentz

[57] ABSTRACT

A method is provided for simultaneously hydrolyzing and hydrogenating compounds containing one six-membered acetal ring and one aldehyde functional group with a water insoluble strongly acid ion exchange resin and a nickel hydrogenation catalyst.

8 Claims, No Drawings

ONE-STEP METHOD FOR HYDROLYZING AND HYDROGENATING ACETAL-ALDEHYDES

CROSS REFERENCE TO RELATED APPLICATION

This is a continuation-in-part of copending application Ser. No. 494,292, filed Aug. 2, 1974 and now abandoned.

BACKGROUND OF THE INVENTION

This invention relates to a process for hydrolyzing and hydrogenating cyclic acetal-aldehyde compounds in one step.

U.S. Pat. No. 2,808,440 discloses the hydrolysis in the presence of an acidic ion-exchange resin of 2,3-dihydropyran and a second step hydrogenation after removal of the acidic ion-exchange resin in the presence of a hydrogenation catalyst.

U.S. Pat. No. 2,888,492 discloses simultaneous hydrolysis and hydrogenation of acetal aldehydes in the presence of mineral acids as well as acetic acid and as a noble metal. However, in *Reactions of Hydrogen with Organic Compounds over Copper, Chromium Oxide and Nickel Catalysts* by Homer Adkins, p. 75, it is disclosed that acetal groups form ether linkages on hydrogenation.

As disclosed in *Organic Chemistry* by Fieser and Fieser, 1957, p. 157, it is also well known that aldehydes condense in the presence of acids to yield high molecular weight resinous materials. Since, chemically, the six-membered acetal ring can also be described as a masked aldehyde, it can be expected that acetal-aldehydes would polymerize in the presence of an acid to yield polymeric resinous materials. Depending on the strength of the acid, the acetal-aldehyde would be expected to condense to a greater or lesser degree, producing higher degrees of polymerization in the presence of strong acids. In addition, some important hydrogenation catalysts such as Raney nickel are attacked by acids, particularly strong acids.

U.S. Pat. No. 3,578,609 and British Pat. No. 1,236,615 disclose the preparation and use of dual function catalysts in which metals are deposited on ion-exchange resins. However, when these catalysts are applied to acetals the expected conversion of the acetal groups to ether linkages is observed.

SUMMARY OF THE INVENTION

It has now been found that organic compounds containing one six-membered acetal ring and one aldehyde group can be hydrolyzed and hydrogenated in a single step to yield the corresponding polyols in an aqueous medium in the presence of hydrogen and a catalyst system of a hydrolytic amount of a strongly acid water insoluble ion-exchange resin and a catalytic amount of a hydrogenation nickel or nickel compound catalyst. If desired, the reaction may be allowed to continue beyond the polyol formation to achieve cyclization of any polyols found which are capable of cyclizing in the presence of a strond acid, such as, for example, the cyclization of 1,4-butanediol (BAD) to tetrahydrofuran (THF).

DETAILED DESCRIPTION OF THE INVENTION

As used herein, the term polyol is intended to include diols as well as tri- and higher hydroxy containing compounds.

The acetal-aldehydes which may be hydrolyzed, hydrogenated and, if desired, cyclized in accordance with this invention contain one six-membered acetal ring and one aldehyde functional group attached to the acetal ring directly or, indirectly, through a cyclic or acyclic, saturated or unsaturated group which is, in turn, attached to the acetal ring at the carbon atom which separates the oxygen atoms in the acetal ring.

The acetal-aldehydes to be processed in accordance with this invention have the general formula

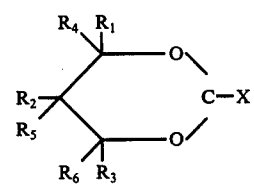

X is

in which M is an alkyl group having 1 to 20 carbon atoms, preferaly 3 carbon atoms, with the proviso that the

group, may be attached to any M carbon atom having a replaceable hydrogen; and $R_1$, $R_2$, $R_3$, $R_4$, $R_5$ and $R_6$ may be the same or different and may be hydrogen or an alkyl group having 1 to 20 carbon atoms, and preferably hydrogen or methyl.

Although alkyl groups having more than 20 carbon atoms can also be used as M and $R_1$, $R_2$, $R_3$, $R_4$, $R_5$ and $R_6$, the upper limit of 20 carbon atoms is preferred to preclude too high a molecular weight. The alkyl groups may also contain any substituents which will not interfere with the hydrolysis-hydrogenation reaction of the invention.

Representative examples of acetal-aldehydes which may be hydrolyzed and hydrogenated in accordance with this invention include

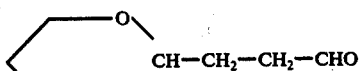

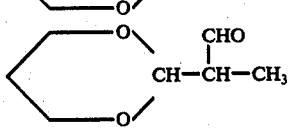

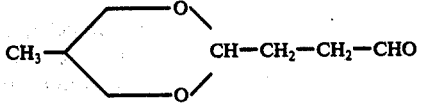

-continued

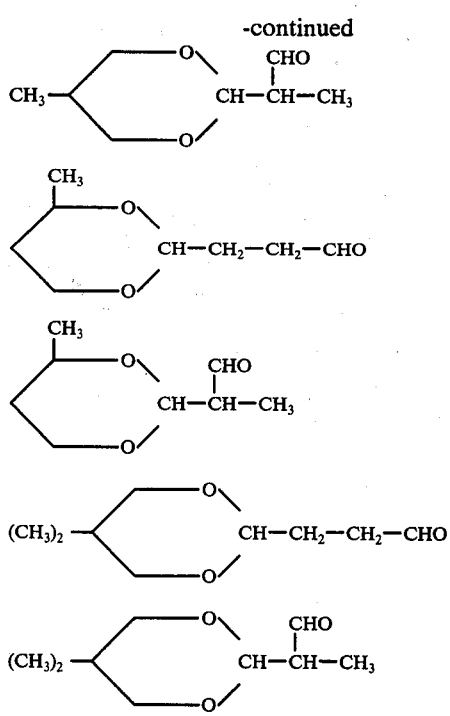

The catalytic liquid hydrolysis-hydrogenation reaction of this invention is carried out in an aqueous medium at elevated temperature under superatmospheric hydrogen pressure. Generally a molar ratio of water to the acetal-aldehyde of 1:1 to 100:1, preferably 1:1 to 10:1, at a hydrogen pressure of 500 to 10,000 psig, preferably 1,000 to 5,000 psig and a temperature of 65° to 150° C are employed.

Any strongly acidic water insoluble ion-exchange resin can be used in the practice of this invention. Typical such resins are those containing sulfonic acid groups such as the resins disclosed in U.S. Pat. No. 2,366,007 which include sulfonated styrene-divinyl benzene copolymeres commercially available as Dowex MSC-1, 50 and 50 WX8; Amberlyst 15, Duolite C-20and the like resins. Other suitable cationexchange resins include, for example, the phenol sulfonic acid-formaldehyde reaction products. Optionally small amounts of basic resins can be used to absorb any slight amount of soluble acid components that may be present in fresh ion-exchange resins. This serves to reduce catalyst corrosion due to acid attack and in no way influences the process.

Any of the metal or metal compound catalysts of the type well known and customarily referred to in the art as hydrogenation catalysts can be used. It is desirable to employ as the hydrogenation catalyst a metal or a compound of a metal which may be easily and economically prepared, which has a high degree of activity, and which retains its activity under the conditions of the process for a length of time sufficient to avoid the necessity of reactivating or replacing the catalyst at too frequent intervals. Generally speaking, hydrogenation catalysts which may be advantageously employed in the execution of the process of the invention are the base metal hydrogenation catalysts. However, because of the case and economy with which it may be prepared and the tendency to be attacked by strong acid solutions, the pyrophoric base metal hydrogenation catalyst, nickel, is advantageous by utilization in the present invention. Most important are nickel-aluminum alloys which are activated by partial removal of the aluminum with NaOH. The hydrogenation catalyst may be employed in a finely divided form and dispersed in and throughout the reaction mixture, or it may be employed in a more massive state, either in essentially the pure state or supported upon or carried by an inert or catalytically active supporting or carrier material, such as pumice, kieselguhr, diatomaceous earth, clay, alumina, charcoal, carbon, or the like, and the reaction mixture contacted therewith as by flowing the mixture over or through a bed of the catalyst or according to other methods that are known in the art.

The insoluble resin and the hydrogenation catalyst which form the catalyst system of this inventionn may exist in various interrelationships with one another as desired but typically a weight ratio of insoluble resin to hydrogenation catalyst of 0.1:1 to 100:1, preferably 1:1 to 10:1 is used.

Depending on the product desired and the kind of reaction system employed (slurry, fixed bed and so on), and hydrolytic-catalytic amount of the catalyst system of this invention may be employed. Generally, amounts of the acid-catalyst system are employed such that 1% by weight of hydrogenation catalyst based on the weight of the acetalaldehyde is present. In a slurry system 1 to 10% by weight based on the contents of the reactor are optimum and in a fixed bed reactor, 10 to 20 times as much may be used.

The reaction of this invention may be carried out either continuously or batchwise. In either case, the time during which the reactor contents are in contact with the catalyst system depends on the product desired. By manipulating temperature and contact time, one may produce either polyol product or the cyclized form of any polyol which is capable of being cyclized in a strongly acid medium or any combination thereof. As temperature and contact time increase, the cyclization reaction is favored. Taking BAD as an example, greater than 90% yields of cylized BAD (THF) can be obtained at higher temperatures and contact times while 99% yields of BAD can be obtained at lower temperatures and contact times. Any interrelationship between temperature and contact time of up to 3 hours at 60° C and up to one half hour at 150°C can be observed. At 130° C or higher, THF forms very rapidly and preferentially. Other methods for producing THF using cation-exchange resins are disclosed in U.S. Pat. No. 3,467,679 and German Pat. No. 850,750.

The polyols produced by the process of this invention may be used for any application for which polyols are suitable such as reactants with isocyanates to form urethanes and polyurethanes, with acids to form esters and polyesters and so on.

The invention is further illustrated but is not intended to be limited by the following examples in which all parts and percentages are by weight unless otherwise specified.

EXAMPLE 1

A 300 ml stirred autoclave is charged with:

| | |
|---|---|
| isomeric mixture of 2 (β and γ formyl ethyl)-5,5-dimethyl-1,3-dioxane (70% of γ) | 50 grams |
| water | 50 grams |
| Raney nickel (wet solids) | 5 grams |
| Dowex 50WX8 | 10 grams |
| Dowex 21K | 1 gram |

The autoclave is then sealed, pressurized with hydrogen and maintained at 1500 psig of hydrogen pressure at 90° C for 30 minutes. At the end of this time, gas chromatograph analysis shows that 95% of the dioxane is converted to a mixture of glycols. A 97% yield of 1,4-butanediol (BAD) is obtained and only trace amounts of tetrahydrofuran (THF) are present.

EXAMPLE 2

A 300 ml stirred autoclave is charged with the formyl dioxane mixture of Example 45 grams

| water | 50 grams |
|---|---|
| Raney nickel (wet solid) | 5 grams |
| Dowex 50WX8 resin | 10 grams |

The autoclave is sealed, pressurized with hydrogen and maintained at 1500 psig of hydrogen pressure at 100° C for 25 minutes. At this point a gas chromatograph scan shows essentially complete conversion of the dioxane essentially to 1,4-butanediol. The temperature is raised to 120° C and maintained fo 30 minutes. At the increased temperature, 60% of the 1,4-butanediol is converted to THF.

EXAMPLE 3

Example 1 is repeated except that the quantity of Dowex 50WX8 resin is increased from 10 to 20 grams. At the end of 30 minutes, 100% of the dioxane is converted. Gas chromatograph analysis shows that the product contains 15% of the THF based on the concentration of 1,4-butanediol in the final mixture.

EXAMPLE 4

Example 1 is repeated except that the quantity of Raney nickel is increased from 5 to 12 grams. Substantially the same results are obtained as reported in Example 1.

EXAMPLE 5

A continuous process is carried out as follows: The autoclave is charged with:

| Ethylene glycol | 30 grams |
|---|---|
| Water | 30 grams |
| Raney Nickel (wet solid) | 5 grams |
| Dowex 50WX8 resin | 10 grams |
| Dowex 21K resin | 0.5 gram |

The autoclave is then sealed and the pressure and temperature adjusted to 1600 psig and 90° C maintained at those levels. An isomeric mixture of 2-($\beta,\gamma$-formyl ethyl)- 5,5-dimethyl-1,3-dioxane (60% $\gamma$) is then pumped into the autoclave at a rate of 60 grams per 40 minutes. A sample taken at 40 minutes shows that the conversion of dioxane is 80% at this point. After the feed is completed the reaction is allowed to continue for 30 minutes. At the end of this period the dioxane conversion to glycols is 97%. At this point the nickel is removed and the reaction mixture heated to 140° C in a still to convert all the 1,4-butanediol to THF which is distilled off overhead. The yield of THF based on the $\gamma$ isomer in the dioxane charged is 91%.

EXAMPLE 6

To a stirred 300 cc autoclave is added the following:

| 2($\beta$, $\gamma$ formyl ethyl)-5-methyl-1,3-dioxane (80% $\gamma$) | 50 grams |
|---|---|
| Water | 50 grams |
| Dowex MSC-1 Resin (a sulfonic acid ion exchange resin) | 15 grams |
| Nickel (Raney, wet solids) | 10 grams |

The temperature is raised to 130° C and the pressure to 2000 psig. At the end of one hour under these conditions the conversion of the dioxanes is complete. The 1,4-butanediol produced is cyclized to THF to the extent of 93%. The yield of THF and butanediol based on the amount of $\gamma$ formyl ethyl isomer charged is 97%.

It is to be understood that any of the components and conditions mentioned as suitable herein can be substituted for its counterpart in the foregoing examples and that similar advantageous results can be expected. Further although the invention has been described in considerable detail in the foregoing, such detail is solely for the purpose of illustration. Variations may be made in the invention by those skilled in the art without departing from the spirit and scope of the invention except as set forth in the claims.

What is claimed is:

1. A one-step process for the hydrolysis and hydrogenation of a cyclic acetal-aldehyde of the general formula

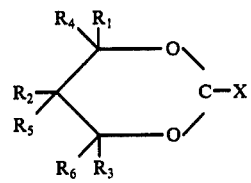

wherein
X is

in which M is alkyl of 1 to 20 carbon atoms and $R_1$, $R_2$, $R_3$, $R_4$, $R_5$ and $R_6$ are the same or different hydrogen or alkyl of 1 to 20 carbon atoms which comprises contacting the cyclic acetal-aldehyde with the combination of hydrogen, water at a molar ratio of water to acetal-aldehyde of 1:1 to 100:1, separate solid particles of a strongly acid water insoluble ion-exchange resin and a catalytic amount of a nickel hydrogenation catalyst, said ion-exchange resin to nickel catalyst weight ratio being 0.1:1 to 100:1 at a temperature of from 65° to 150° C and a hydrogen pressure of from 500 to 10,000 psig to form the corresponding polyol.

2. The process of claim 1 wherein the hydrogenation catalyst is Raney nickel.

3. The process of claim 1 wherein the insoluble resin is a sulfonated styrene-divinyl benzene copolymer.

4. The process of claim 1 wherein M is an alkyl group containing 3 carbon atoms.

5. The process of claim 1 wherein $R_1$, $R_2$, $R_3$, $R_4$, $R_5$ and $R_6$ are hydrogen or methyl.

6. The process of claim 4 wherein $R_1$, $R_2$, $R_3$, $R_4$, $R_5$ and $R_6$ are hydrogen or methyl.

7. The process of claim 1 wherein the cyclic acetal-aldehyde is 2(2'-propanal)-5-methyl dioxane.

8. The process of claim 1 wherein the cyclic acetal-aldehyde is 2(3'-propanal)-5-methyl dioxane.

UNITED STATES PATENT OFFICE
CERTIFICATE OF CORRECTION

PATENT NO. : 4,044,059
DATED : AUGUST 23, 1977
INVENTOR(S) : HARRY BUGBIRD COPELIN

It is certified that error appears in the above-identified patent and that said Letters Patent are hereby corrected as shown below:

Column 1, line 24, after "and" delete "as".

Column 1, line 65, "found" should be -- formed --.

Column 1, line 66, "strond" should be -- strong --.

Column 2, line 33, "preferaly" should be -- preferably --.

Column 3, line 41, "copolymeres" should be -- copolymers --.

Column 3, line 63, "case" should be -- ease --.

Column 4, line 21, "and" should be -- any --.

Column 5, line 11, after "Example" add -- 1 --.

Column 5, line 32, after "of" delete -- the --.

Signed and Sealed this

Seventh Day of February 1978

[SEAL]

Attest:

RUTH C. MASON
Attesting Officer

LUTRELLE F. PARKER
Acting Commissioner of Patents and Trademarks